(12) United States Patent
    Bristow

(10) Patent No.: US 10,364,225 B2
(45) Date of Patent: Jul. 30, 2019

(54) PROCESS FOR PREPARING BOSCALID

(71) Applicant: JIANGSU ROTAM CHEMISTRY CO., LTD, Jiangsu (CN)

(72) Inventor: James Timothy Bristow, Chai Wan (HK)

(73) Assignee: JIANGSU ROTAM CHEMISTRY CO., LTD., Jiangsu (CN)

( * ) Notice: Subject to any disclaimer, the term of this patent is extended or adjusted under 35 U.S.C. 154(b) by 0 days.

(21) Appl. No.: 16/099,610

(22) PCT Filed: Jan. 9, 2017

(86) PCT No.: PCT/CN2017/070635
§ 371 (c)(1),
(2) Date: Nov. 7, 2018

(87) PCT Pub. No.: WO2017/193619
PCT Pub. Date: Nov. 16, 2017

(65) Prior Publication Data
US 2019/0144392 A1    May 16, 2019

(30) Foreign Application Priority Data
May 9, 2016 (GB) .................................. 1608083.0

(51) Int. Cl.
*C07D 213/82* (2006.01)
*A01N 43/40* (2006.01)

(52) U.S. Cl.
CPC ............ *C07D 213/82* (2013.01); *A01N 43/40* (2013.01)

(58) Field of Classification Search
CPC ................................................... C07D 213/82
USPC ........................................................ 546/316
See application file for complete search history.

(56) References Cited

U.S. PATENT DOCUMENTS

| 7,087,239 B2 | 8/2006 | Bratz et al. |
| 7,501,384 B2 | 3/2009 | Mayer et al. |
| 2004/0249164 A1 | 12/2004 | Bratz et al. |
| 2006/0154825 A1 | 7/2006 | Mayer et al. |

FOREIGN PATENT DOCUMENTS

| CN | 1558901 A | 12/2004 |
| CN | 1751026 A | 3/2006 |
| CN | 103980192 A | 8/2014 |
| GB | 2536979 A | 10/2016 |
| GB | 2539022 A | 12/2016 |

OTHER PUBLICATIONS

International Search Report and Written Opinion regarding International Application No. PCT/CN2017/070635 dated Apr. 13, 2017.
Combined Search and Examination Report regarding Application No. GB1608083.0 dated Feb. 15, 2017.

*Primary Examiner* — Patricia L Morris
(74) *Attorney, Agent, or Firm* — Dickinson Wright PLLC

(57) ABSTRACT

A process for preparing the polymorph I of the anhydrate of 2-Chloro-N-(4'-chlorobiphenyl-2-yl)-nicotinamide (boscalid) of the formula I:

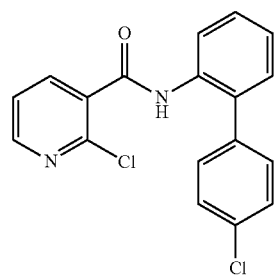

I is provided. The process comprises the steps of:
  a) dissolving the polymorph II of the anhydrate of boscalid in a first solvent in an amount and at conditions allowing dissolution of the polymorph II of the anhydrate of boscalid;
  b) combining the resulting solution with water;
  c) isolating the solid from the solvent mixture; and
  d) drying the solid to obtain the polymorph I of the anhydrate of boscalid.

16 Claims, 2 Drawing Sheets

PROCESS FOR PREPARING BOSCALID

CROSS REFERENCE TO RELATED APPLICATIONS

The present application is a 371 national phase entry of PCT/CN2017/070635, filed on 9 Jan. 2017, which claims the priority of GB Patent Application No. 1608083.0, filed on May 9, 2016, the contents of which are incorporated herein by reference in their entirety.

FIELD

The present invention relates to a process for preparing a specific polymorphic form of the anhydrate of 2-Chloro-N-(4'-chloro-bi-phe-nyl-2-yl)-nicotinamide (boscalid). In particular, the present invention relates to a process for preparing polymorph I of the anhydrate of boscalid.

BACKGROUND

2-Chloro-N-(4'-chlorobiphenyl-2-yl)-nicotinamide, having the common name boscalid, is a compound with the structural formula I:

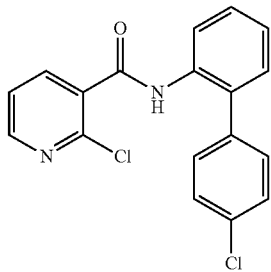

I

Boscalid is a fungicide of the carboxamide group and acts as a succinate dehydrogenase inhibitor (SDHI), a respiratory inhibitor of mitochondria. It was first registered for commercial use in 2003 and is now registered in over 50 countries including Europe and America.

EP 0545099 discloses nicotinamides, anilide derivatives and 2-aminobiphenyl derivatives and their use for controlling *Botrytis*. The subject compounds are defined by way of a Markush formula.

U.S. Pat. No. 7,241,896 concerns a process for producing 2-halogen-pyridine-carboxylic acid amides. The preparation of boscalid is disclosed and exemplified. Boscalid is synthesized by the reaction of 2-chloro-3-nicotinyl chloride II with 2-(4-chlorophenyl)aniline in a solvent system. Boscalid was crystallized by cooling an organic solution, after extraction with sodium carbonate solution. Examples of water-immiscible organic solvents indicated in U.S. Pat. No. 7,241,896 include aromatic, aliphatic and cycloaliphatic hydrocarbons, aromatic, aliphatic and cycloaliphatic halogenated hydrocarbons, acyclic ethers, preferably having from 4 to 10 carbon atoms, esters having from 3 to 10 carbon atoms, preferably those of aliphatic or cycloaliphatic alcohols preferably with aliphatic carboxylic acids, for example esters of acetic acid, propionic acid or butyric acid with $C_3$ $C_8$ alkanols, such as methyl, ethyl, n-propyl, n-butyl or isobutyl acetate, propionate, butyrate, and the like, ketones, preferably having from 4 to 10 carbon atoms, such as methyl ethyl ketone, and also aliphatic nitriles preferably having from 4 to 10 carbon atoms, such as butyronitrile, as well as mixtures of the aforementioned organic solvents. Xylene appears to be the preferred solvent of U.S. Pat. No. 7,241,896.

U.S. Pat. No. 8,350,046 discloses a process for preparing arylcarboxamides by reacting an acid chloride with an arylamine in a non-aqueous solvent. Toluene appears to be the preferred solvent of U.S. Pat. No. 8,350,046.

U.S. Pat. No. 7,087,239 concerns crystalline hydrates of nicotinic acid anilide and benzoyl anilide derivatives. The synthesis and recovery of the hydrate of boscalid is specifically exemplified in U.S. Pat. No. 7,087,239. The hydrate is obtained by first preparing the anhydrate of boscalid, which is obtained at the end of the synthesis procedure as a solution in hot xylene. Upon cooling, boscalid crystallized from the solution and was dried under vacuum in an oven. The anhydrate is indicated to have the following physical properties:

| | |
|---|---|
| Molecular weight [g/mol]: | 343.2 |
| Melting point [° C.] (DSC): | 145.2 |
| Density [g/mol]: | 1.42 |
| X-ray reflection (2θ degree): | 18; 22.5; 9.5; 6 |
| Cu-Kα | |
| IR absorption [cm−1]: | 1650 |
| Water content [%]: | <1 |

U.S. Pat. No. 7,087,239 discloses that the hydrate can be formed by dissolving the anhydrate in tetrahydrofuran (THF) at 40° C. and the resulting solution added to water. The precipitate was removed by filtration and dried, to yield the monohydrate of boscalid. The crystalline modification of the anhydrate of boscalid disclosed in U.S. Pat. No. 7,087,239 is referred to herein as the polymorph I of the anhydrate of boscalid.

U.S. Pat. No. 7,501,384 discloses an allegedly novel crystalline modification of the anhydrate of boscalid. The crystalline modification disclosed in U.S. Pat. No. 7,501,384 is referred to herein as the polymorph II of the anhydrate of boscalid. It is suggested in U.S. Pat. No. 7,501,384 that the polymorph II of the anhydrate of boscalid is more suitable for making formulations which require grinding/milling processes.

U.S. Pat. No. 7,501,384 describes that the polymorph II of the anhydrate of boscalid may be prepared by a process comprising:
a) dissolving the polymorph I of the anhydrate of boscalid in a polar organic solvent or an aromatic hydrocarbon; and
b) precipitation of the polymorph II of the anhydrate of boscalid by cooling the solvent.

An alternative process for the preparation of the polymorph II of the anhydrate of boscalid disclosed in U.S. Pat. No. 7,501,384 comprises:
a) heating the polymorph I of the anhydrate of boscalid to above 150° C. until melted; and
b) cooling the melt with the addition of seed crystals of the polymorph II of the anhydrate of boscalid.

U.S. Pat. No. 7,501,384 describes the polymorph II of the anhydrate of boscalid as having the following properties:

| | |
|---|---|
| Molecular weight [g/mol]: | 342 |
| Melting point [° C.] (DSC): | 147.2 |
| Heat of fusion [J/g] (DSC): | 106 |
| Density [g/cm³]: | 1.457 |

| Characteristic IR bands [cm$^{-1}$]: | 868, 917, 1675 |

The cell parameters from the crystallographic investigations of the polymorph II of the anhydrate of boscalid using a single crystal diffractometer from Siemens are given in U.S. Pat. No. 7,501,384 as follows:

| Class: | Monoclinic |
|---|---|
| Space group: | P21/c |
| a: | 1162.5(6) pm |
| b: | 1134.2(4) pm |
| c: | 1283.2(5) pm |
| α: | 90° |
| β: | 114.52(4)° |
| γ: | 90° |
| Volume: | 1.5390 nm$^{-3}$ |
| Z: | 4 |
| Density (calculated): | 1.481 mg/m$^{-3}$ |
| R$^1$, wR$^2$: | 0.0489; 0.1264 |

The parameters indicated above have the following meanings:

a, b, c=edge lengths of the unit cell;
α, β, γ=corresponding angles; and
Z=number of molecules in the unit cell.
FTIR spectrometry may be used to record IR spectra.

SUMMARY

Conventionally, the polymorph I of the anhydrate of boscalid is prepared from a solution in xylene. Xylene has a high boiling point and a high toxicity.

Hence, there is a need in the art to provide an improved process for preparing the polymorph I of the anhydrate of boscalid, preferably a process that avoids the shortcomings of the prior art processes, in particular the reliance on a solvent such as xylene.

A novel process for the preparation of the polymorph I of the anhydrate of boscalid has now been found.

Accordingly, the present invention provides a process for preparing the polymorph I of the anhydrate of 2-Chloro-N-(4'-chlorobiphenyl-2-yl)-nicotinamide (boscalid) of the formula I:

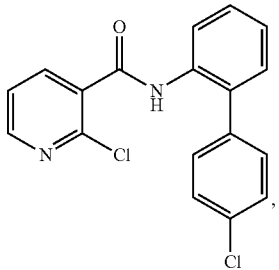

the process comprising the steps of:
a) dissolving the polymorph II of the anhydrate of boscalid in a first solvent in an amount and at conditions allowing dissolution of the polymorph II of the anhydrate of boscalid;
b) combining the resulting solution with water;
c) isolating the solid from the solvent mixture; and
d) drying the solid to obtain the polymorph I of the anhydrate of boscalid.

In the first step of the process of the present invention, a solution of boscalid is formed by dissolving in a first organic solvent the polymorph II of the anhydrate of boscalid. The first solvent is an organic solvent. Suitable solvents of boscalid for use as the first solvent include ethers, preferably linear or cyclic lower ethers (that is ethers having from 1 to 12 carbon atoms), more preferably linear or cyclic $C_2$ to $C_6$ ethers, such as tetrahydrofuran (THF), methylether, methylethylether or ethylethylether; ketones, preferably $C_2$ to $C_6$ ketones, such as acetone, propanone, or butanone; esters, preferably linear $C_2$ to $C_6$ esters, such as ethyl acetate, methyl acetate or propyl acetate; dimethyl formamide (DMF); alcohols, preferably straight or branched $C_1$ to $C_8$ aliphatic alcohol, more preferably at least one straight or branched $C_1$ to $C_4$ aliphatic alcohol, such as methanol, ethanol, propanol, n-butanol; acetonitrile; aromatic hydrocarbons, preferably substituted with one or more substituents, which may be the same or different, selected from the group consisting of alkyl, optionally substituted by one or more halogens, which may be the same or different, nitro, halogen, ether, and the like such as benzene, toluene, or chlorobenzene; halogenated alkanes; and mixtures thereof. Preferred halogenated alkanes are mono- or di-substituted alkanes. Chloride moieties are preferred substituents for the alkanes. The halogenated alkanes are preferably lower alkanes (that is alkanes having from 1 to 12 carbon atoms), more preferably $C_1$ to $C_6$ halogenated alkanes, such as mono- or di-chloromethane, mono- or 1,1-dichloro- or 1,2-di-chloroethane, mono- or 1,1-di-chloro, or 1,2-dichloro- or 1,3 di-chloropropane.

Ketones are particularly preferred as the first solvent, especially acetone. Esters are also preferred as the first solvent, especially ethyl acetate; alcohols are also preferred, especially methanol; aromatic hydrocarbons are also preferred, especially toluene; ethers are also preferred as the first solvent, especially tetrahydrofuran.

Other preferred solvents include acetonitrile and dimethyl formamide (DMF).

The polymorph II of the anhydrate of boscalid is dissolved in an amount of the first solvent under conditions allowing complete dissolution of the polymorph I of the anhydrate of boscalid. The dissolution in step a) may be carried out at any suitable temperature. If an elevated temperature is employed in step a), the temperature is below the boiling point of the first solvent. Optionally, for example depending on the type and the amount of the solvent used, dissolution of the polymorph II of the anhydrate of boscalid may be carried out by heating the solvent to elevated temperatures. A minimum temperature of 20° C. may be used, preferably at least 30° C., more preferably at least 40° C. Depending upon the solvent system being used, the temperature may be up to 90° C., preferably up to 85° C., more preferably up to 80° C., still more preferably up to 75° C. Suitable temperatures are a temperature of from 20 to 90° C., preferably from 30 to 90° C., more preferably from 30 to 80° C., even more preferably from 40 to 70° C., more preferably still to a temperature of from 40 to 60° C.

The dissolution of the polymorph II of the anhydrate of boscalid in the first solvent may be carried out with agitation, preferably with stirring and/or shaking.

Once the polymorph II of the anhydrate of boscalid has been fully dissolved in the first solvent, the resulting solution is combined with a second solvent in step b) of the process. In the present invention, the second solvent is water.

The combination of water to the solution of boscalid is preferably effected in a slow manner, such as dropwise. The combination may be carried out stepwise or continuously. The water is preferably combined with the boscalid solution with agitation, for example stirring, to avoid a local high concentration of the boscalid solution. The solution of boscalid may be added to the water. More preferably, the water is added to the solution of boscalid.

Water is employed in step b) in an amount until precipitation of a solid commences and is preferably continued to achieve full precipitation of the solid boscalid from the solution.

Water may be employed in any suitable amount to effect precipitation of boscalid from the solution. Preferably, water is employed in step b) in an amount sufficient to cause substantially complete precipitation of solid boscalid from the solution. For example, water may be used in an amount by weight equal to the amount by weight of the first solvent used in step a).

Water may be combined with the solution prepared in step a) at any suitable temperature below the boiling point of water. A lower temperature of 10° C. is suitable, preferably 15° C., more preferably at least 20° C., still more preferably at least 30° C., more preferably still at least 40° C. An upper temperature of 85° C. is suitable, preferably 75° C., more preferably 70° C., still more preferably 75° C., more preferably still up to 70° C. A temperature in the range of from 10 to 85° C. is suitable, preferably from 15 to 75° C., more preferably from 20 to 65° C. Preferably, step b) is conducted at a temperature in the range of from 30 to 60° C., more preferably from 40 to 55° C., especially from 50 to 55° C.

Adjusting the temperature of the solution of the polymorph II of the anhydrate of boscalid in the first solvent is required to the extent that the temperature of step b) of the process is above or below the temperature of the solution resulting in step a). Preferably, the temperature in step a) of the process at which dissolution is effected is above the temperature or at least equal to the temperature in step b).

This may be achieved in a number of ways. For example, the temperature of the solution resulting from step a) may be adjusted, as required, during step b) before combination with water. In one convenient processing scheme, the boscalid solution in step a) is formed at the same temperature as water used in step b).

The solution of the polymorph II of the anhydrate of boscalid produced in step a) may be adjusted at any suitable rate, if required. Preferably adjusting the temperature in step b) is carried out at a rate of from about 1 to 20° C./minute, more preferably from 1 to 10° C./minute, still more preferably from about 5 to 10° C./minute. Preferably adjusting is carried out while agitating the solution, for example by stirring.

After the solution has reached the desired temperature in step b), this temperature is preferably maintained at the selected level for a time period sufficient to ensure a uniform temperature throughout the solution.

Alternatively, the solution resulting from step a) may be adjusted by first adjusting the temperature of the water to an appropriate temperature, before it is combined with the solution. For example, the water may be at a temperature lower than the temperature of the solution produced in step a) and thereby cool the solution when added thereto.

Preferably, both the temperature of the boscalid solution resulting from step a) is adjusted, as required to be within the temperature range in step b) discussed above and the temperature of the second solvent is adjusted to be within the aforementioned range. In this way, both the boscalid solution and the second solvent are at a temperature in the aforementioned range when combined in step b) of the process. Preferably, the temperature of the boscalid solution and the temperature of the water are substantially the same when being combined.

Preferably, after complete combination of the boscalid solution resulting from step a) with water, the resulting mixture is maintained within the temperature range in step b) discussed above for any suitable time period, in particular from 10 to 60 minutes, preferably from 15 to 50 minutes, more preferably from 20 to 40 minutes, particularly about 30 minutes. Thereafter, the resulting mixture is cooled, for example to a temperature of from 20 to 25° C. Preferably, the resulting mixture is maintained at this temperature after cooling, for example for 1 to 3 hours, to allow for complete precipitation of the boscalid solid.

The solid precipitated from the solution in step b) of the process may then be recovered in any suitable manner, such as by one or more of decanting the solvent, filtration, and/or evaporation of the solvent.

The solid of boscalid recovered in step c) is then dried in step d), for example under reduced pressure, preferably under a vacuum. Suitable drying techniques are known in the art. Due to the use of water as the second solvent in step b), the boscalid solid precipitated is hydrated. Drying of the precipitate is therefore carried out to a sufficient extent to produce a substantially anhydrous solid product. Suitable drying temperatures are, for example, from 40 to 80° C., more preferably from 50 to 70° C., still more preferably from 55 to 60° C. Suitable drying periods are, for example, up to 5 hours or longer, such as up to 6 hours or 8 hours, in particular from 8 to 10 hours. The drying time will vary according to the drying conditions and the drying technique employed.

During the process of preparing the polymorph I of the anhydrate of boscalid, the conversion rate from polymorph II to polymorph I can be monitored using appropriate analysis methods and based on the chemical and physical properties of the two polymorphic forms, some of which are listed in Table 1 below.

TABLE 1

Physical properties of anhydrous boscalid polymorph I and polymorph II

| Properties | Anhydrous boscalid, polymorph I | Anhydrous boscalid, polymorph II |
| --- | --- | --- |
| Molecular weight [g/mol] | 342 | 342 |
| Melting point [° C.] (DSC) | 144.8 | 147.2 |
| Heat of fusion [J/g] (DSC) | 85 | 106 |
| Density [g/cm$^3$] | 1.399 | 1.457 |
| IR characteristic band [cm$^{-1}$] | 924, 1310, 1650 | 868, 917, 1675 |

Any suitable analysis method may be employed. One suitable analysis technique is IR spectroscopy, which also allows for quantification of the conversion, for example by the shifting of a characteristic band, such as the C=O stretching vibration. For example, the C=O stretching vibration shifts from 1675 cm$^{-1}$ to 1650 cm$^{-1}$ when polymorph II of anhydrous boscalid is converted to polymorph I. The disappearance from the IR spectrograph of a band at 1675 cm$^{-1}$ indicates complete conversion from polymorph II to polymorph I.

Alternatively, single-crystal X-ray diffraction may be used for monitoring the conversion. Table 2 below lists cell parameters of the two polymorphic forms.

TABLE 2

Table cell parameters from the crystallographic investigations using a single crystal diffractometer

| Parameters | Anhydrous boscalid, polymorph I | Anhydrous boscalid, polymorph II |
|---|---|---|
| Space group | P21/c | P21/c |
| a | 1479.2(3) pm | 1163.2(8) pm |
| b | 1157.67(19) pm | 1136.3(5) pm |
| c | 1872.1(3) pm | 1287.3(8) pm |
| α | 90° | 90° |
| β | 91.993(17)° | 114.57(1)° |
| γ | 90° | 90° |
| Melting point | 144-145° C. | 147-148° C. |

Where the symbols have the following meaning:
a, b, c=edge length of unit cell;
α, β, γ=corresponding angles; and
Z=number of molecular in unit cell.

The process of the present invention has the advantage of being easy to carry out and is suitable for use on an industrial scale. The process of the present invention also provides the advantage that a reduction in the use of toxic solvents can be obtained, thereby diminishing harm to the environment.

DETAILED DESCRIPTION

Figure 1:
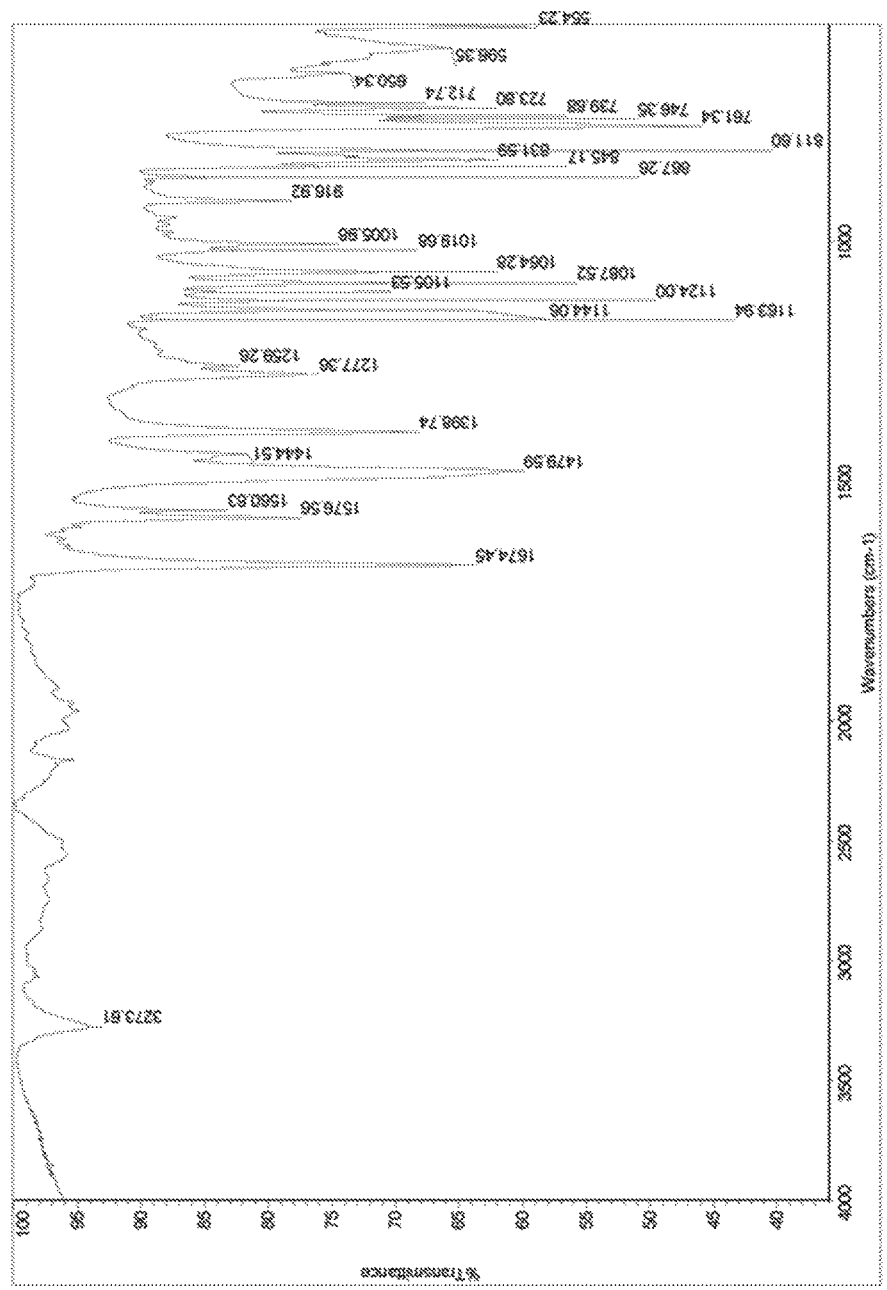
FIG. 1 is the IR spectrum of the polymorph II of the anhydrate of boscalid.
Figure 2:
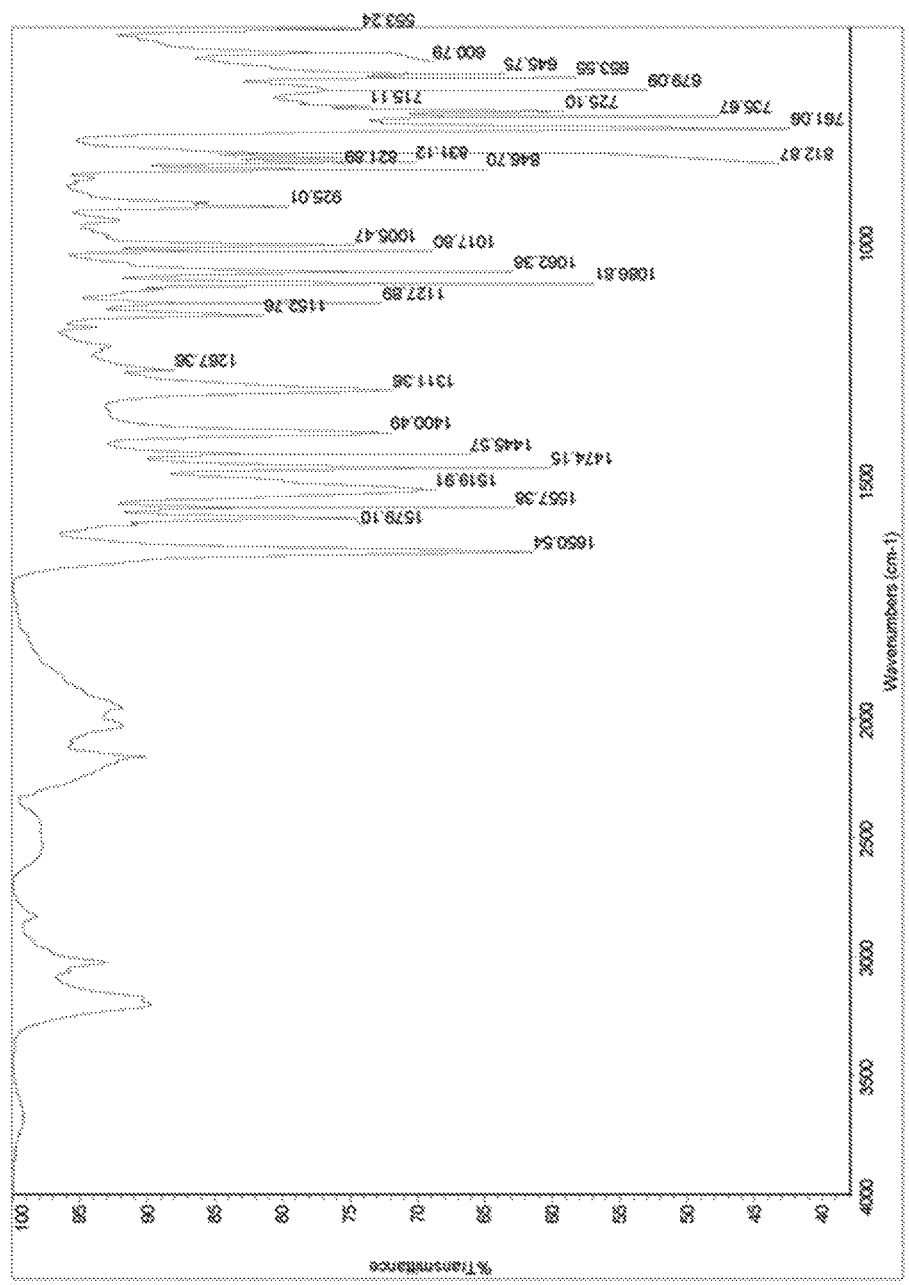
FIG. 2 is the IR spectrum of the polymorph I of the anhydrate of boscalid.

The present invention will be further described, for illustration purposes only, by way of the following examples.

Unless otherwise indicated, percentages are percent by weight.

EXAMPLES

Example 1

Anhydrous boscalid polymorph II (200 g, 0.583 mol) was added to a reaction bottle with the addition of acetone (1000 mL). The mixture was heated to a temperature of from 50 to 55° C. while stirring until the boscalid had dissolved completely. The resulting solution was maintained at a temperature of from 50 to 55° C.

Water (800 mL) was heated to a temperature of from 50 to 55° C. in a reaction bottle and transferred to a dropping funnel.

The water was added dropwise from the dropping funnel to the reaction bottle and combined with the boscalid solution with stirring. Gradually, solid was seen to precipitate from the solution. After the addition of the water had been completed, the resulting mixture was held at a temperature of from 50 to 55° C. for 30 minutes, after which the resulting mixture was cooled to a temperature of from 20 to 25° C. and maintained at this temperature for from 1 to 2 hours. Thereafter, the mixture was filtered and the filter cake was washed with water. The resulting solid was dried at 55 to 60° C. in a vacuum for from 8 to 10 hours. 192 g of white powder with yield of 96% was obtained.

Single-crystal X-ray diffraction and IR spectroscopy were used to identify the solid product as the polymorph I of the anhydrate of boscalid.

Example 2

Anhydrous boscalid polymorph II (200 g, 0.583 mol) was added to a reaction bottle with the addition of dimethyl formamide (1000 mL). The mixture was heated to a temperature of from 85 to 90° C. while stirring until the boscalid had dissolved completely. The resulting solution was cooled and maintained at a temperature of from 50 to 55° C.

Water (1000 mL) was heated to a temperature of from 50 to 55° C. in a reaction bottle and transferred to a dropping funnel.

The water was added dropwise from the dropping funnel to the reaction bottle and combined with the boscalid solution with stirring. Gradually, solid was seen to precipitate from the solution. After the addition of the water had been completed, the resulting mixture was held at a temperature of from 50 to 55° C. for 30 minutes, after which the resulting mixture was cooled to a temperature of from 20 to 25° C. and maintained at this temperature for 1 to 2 hours. Thereafter, the mixture was filtered and the filter cake was washed with water. The resulting solid was dried at a temperature of from 55 to 60° C. in a vacuum for 8 to 10 hours. 168 g of white powder with yield of 84% was obtained.

Single-crystal X-ray diffraction and IR spectroscopy were used to identify the solid product as the polymorph I of the anhydrate of boscalid.

Example 3

Anhydrous boscalid polymorph II (200 g, 0.583 mol) was added to a reaction bottle with the addition of tetrahydrofuran (1000 mL). The mixture was heated to a temperature of from 60 to 65° C. while stirring until the boscalid had dissolved completely. The resulting solution was cooled and maintained at a temperature of from 50 to 55° C.

Water (800 mL) was heated to a temperature of from 50 to 55° C. in a reaction bottle and transferred to a dropping funnel.

The water was added dropwise from the dropping funnel to the reaction bottle and combined with the boscalid solution with stirring. Gradually, solid was seen to precipitate from the solution. After the addition of the water had been completed, the resulting mixture was held at a temperature of from 50 to 55° C. for 30 minutes, after which the resulting mixture was cooled to a temperature of from 20 to 25° C. and maintained for at this temperature for 1 to 2 hours. Thereafter, the mixture was filtered and the filter cake was washed with water. The resulting solid was dried at a temperature of from 55 to 60° C. in a vacuum for from 8 to 10 hours. 168 g of white powder with yield of 84% was obtained.

Single-crystal X-ray diffraction and IR spectroscopy were used to identify the solid product as the polymorph I of the anhydrate of boscalid.

The invention claimed is:

1. A process for preparing the polymorph I of the anhydrate of 2-Chloro-N-(4'-chlorobiphenyl-2-yl)-nicotinamide (boscalid) of the formula I:

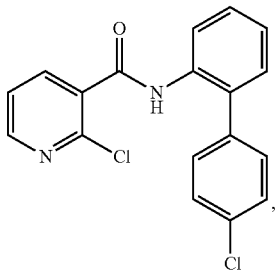

the process comprising the steps of:
a) dissolving the polymorph II of the anhydrate of boscalid in a first solvent in an amount and at conditions allowing dissolution of the polymorph II of the anhydrate of boscalid;
b) combining the resulting solution with water;
c) isolating the solid from the solvent mixture; and
d) drying the solid to obtain the polymorph I of the anhydrate of boscalid.

2. The process according to claim 1, wherein the first solvent is selected from a linear or cyclic lower ether, a ketone, an ester, an alcohol, an aromatic hydrocarbon, a halogenated alkane, dimethyl formamide (DMF), acetonitrile and mixtures thereof.

3. The process according to claim 2, wherein the first solvent is selected from a linear or cyclic $C_2$ to $C_6$ ether, a $C_2$ to $C_6$ ketone, a $C_1$ to $C_6$ halogenated alkane, an aromatic hydrocarbon substituted by one or more halogens, a linear $C_2$ to $C_6$ esters, a straight or branched $C_1$ to $C_4$ aliphatic alcohol, dimethyl formamide (DMF), acetonitrile or a mixture thereof.

4. The process according to claim 3, wherein the first solvent is selected from tetrahydrofuran, acetone, ethyl acetate, dimethyl formamide (DMF), methanol, acetonitrile, toluene, mono- or di-chloromethane, mono- or 1,1-dichloro- or 1,2-di-chloroethane, or mixtures thereof.

5. The process according to claim 1, wherein step a) is conducted at an elevated temperature.

6. The process according to claim 5, wherein step a) is conducted at a temperature of from 20 to 90° C.

7. The process according to claim 6, wherein step a) is conducted at a temperature of from 30 to 90° C.

8. The process according to claim 7, wherein step a) is conducted at a temperature of from 30 to 80° C.

9. The process according to claim 8, wherein step a) is conducted at a temperature of from 40 to 60° C.

10. The process according to claim 1, wherein in step b) the water is added to the solution resulting from step a).

11. The process according to claim 1, wherein step b) is conducted at a temperature of from 20 to 65° C.

12. The process according to claim 11, wherein step b) is conducted at a temperature of from 30 to 60° C.

13. The process according to claim 12, wherein step b) is conducted at a temperature of from 40 to 55° C.

14. The process according to claim 13, wherein step b) is conducted at a temperature of from 50 to 55° C.

15. The process according to claim 1, wherein the temperature of both the solution produced in step a) and the water is adjusted to the temperature required in step b), before being combined.

16. The process according to claim 1, wherein drying is conducted under vacuum at an elevated temperature.

* * * * *